United States Patent
Duan et al.

(10) Patent No.: US 10,770,661 B2
(45) Date of Patent: Sep. 8, 2020

(54) THERMALLY ACTIVATED DELAYED FLUORESCENCE MATERIAL AND APPLICATION THEREOF IN ORGANIC ELECTROLUMINESCENCE DEVICE

(71) Applicants: KUNSHAN GO-VISIONOX OPTO-ELECTRONICS CO., LTD., KunShan, Jiangsu (CN); TSINGHUA UNIVERSITY, Beijing (CN)

(72) Inventors: Lian Duan, Beijing (CN); Dongdong Zhang, Beijing (CN); Song Liu, Beijing (CN); Fei Zhao, Beijing (CN)

(73) Assignees: KUNSHAN GP-VISIONOX OPTO-ELECTRONICS CO., LTD., Kunshan (CN); TSINGHUA UNIVERSITY, Beijing (CN)

( * ) Notice: Subject to any disclaimer, the term of this patent is extended or adjusted under 35 U.S.C. 154(b) by 36 days.

(21) Appl. No.: 15/770,730

(22) PCT Filed: Nov. 30, 2016

(86) PCT No.: PCT/CN2016/107913
§ 371 (c)(1),
(2) Date: Apr. 24, 2018

(87) PCT Pub. No.: WO2017/101675
PCT Pub. Date: Jun. 22, 2017

(65) Prior Publication Data
US 2019/0074447 A1    Mar. 7, 2019

(30) Foreign Application Priority Data

Dec. 18, 2015 (CN) .......................... 2015 1 0957493

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/88* (2013.01); *C07D 241/48* (2013.01);
(Continued)

(58) Field of Classification Search
CPC ........ C07D 209/88; C09K 11/06; H01L 51/50
See application file for complete search history.

(56) References Cited

U.S. PATENT DOCUMENTS 9,815,940 B2   11/2017   Eckes et al.
2016/0181545 A1   6/2016   Stoessel et al.

FOREIGN PATENT DOCUMENTS

CN   102702132 A   10/2012
CN   102709485 A   10/2012
(Continued)

OTHER PUBLICATIONS

Kretzschmar et al., Development of Thermally Activated Delayed Fluorescence Materials with Shortened Emissive Lifetimes, The Journal of Organic Chemistry, vol. 80, No. 18, pp. 9126-9131 (Aug. 20, 2015).*

(Continued)

*Primary Examiner* — Deepak R Rao
(74) *Attorney, Agent, or Firm* — Maschoff Brennan

(57) ABSTRACT

The present invention discloses a thermally activated delayed fluorescence material and application thereof in an organic electroluminescence device. The thermally activated delayed fluorescence material is a compound having the general structure of Formula I or Formula II:

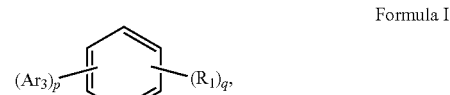

Formula I

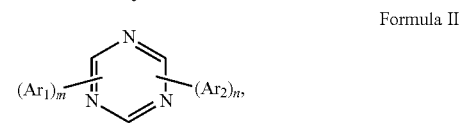

Formula II

In Formula I and Formula II, $R_1$ is a cyano, p is 1, 2 or 3, q is 1, 2 or 3, m is 1 or 2, n is 1 or 2, $Ar_1$ is a phenyl substituted with one or more groups selected from $C_{1-6}$ alkyl, methoxy, ethoxy, or phenyl, $Ar_2$ and $Ar_3$ are selected from the following groups:

(Continued)

-continued
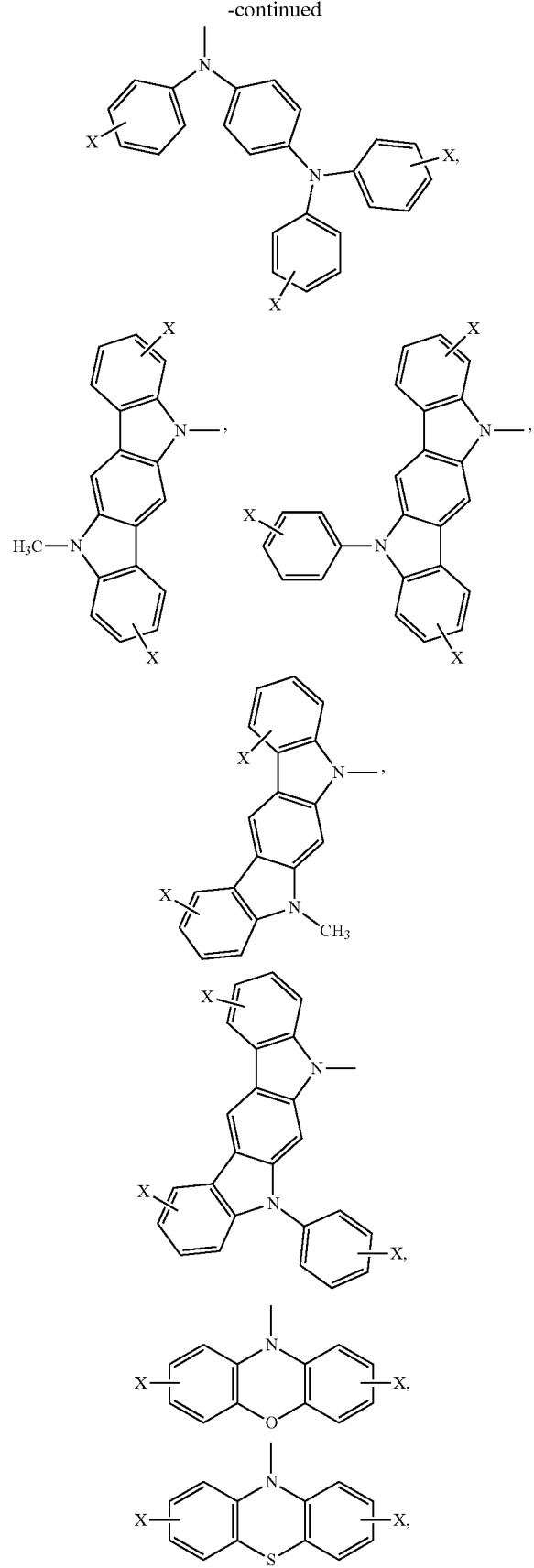
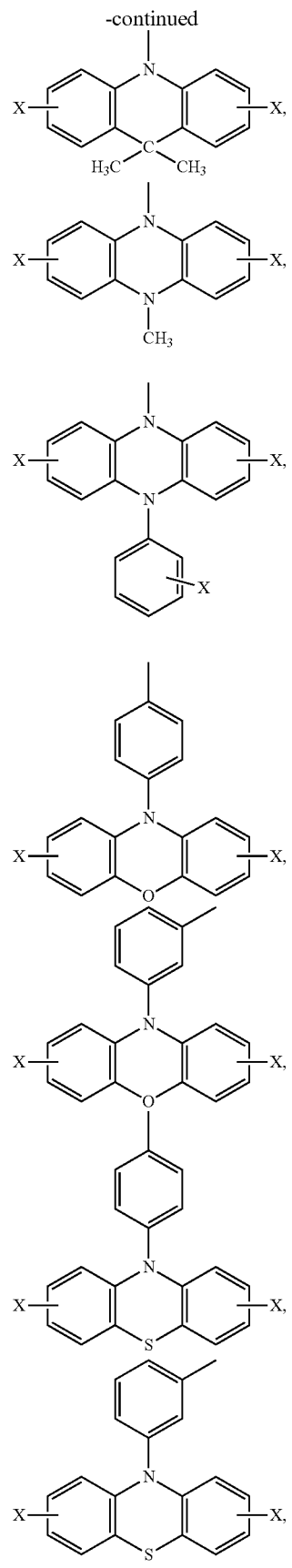

-continued
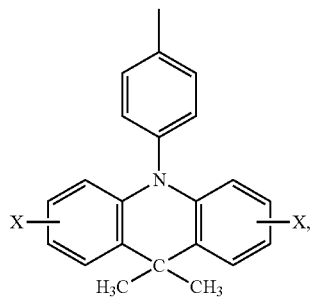
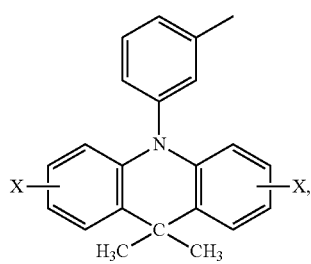
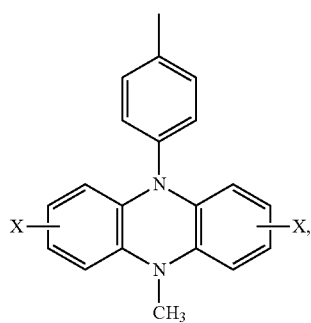
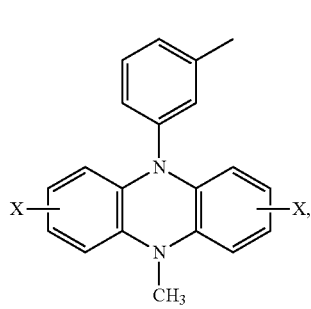
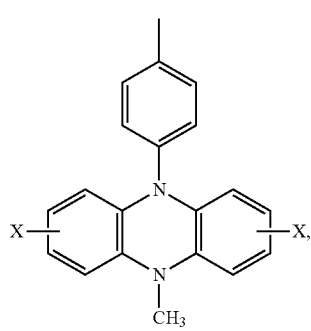
-continued
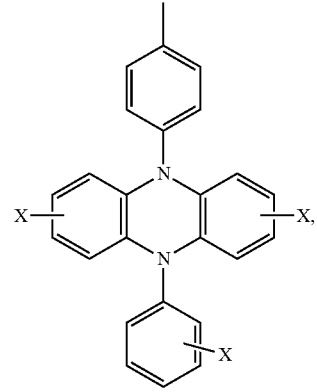
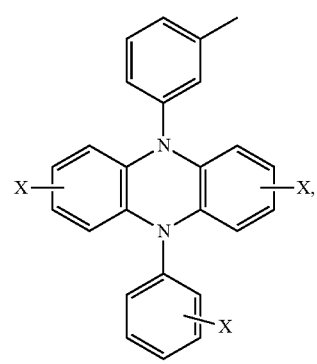
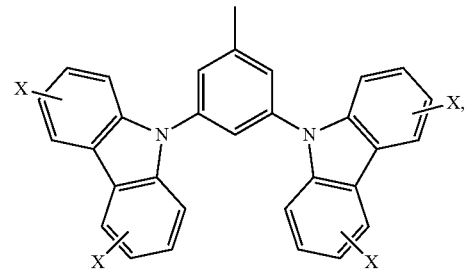
and X is bromine or iodine. The present invention further discloses application of the thermally activated delayed fluorescence material as a host material or a luminescent dye of a luminescent layer of an organic electroluminescence device.
9 Claims, 1 Drawing Sheet
(51) Int. Cl.
*C07D 413/14* (2006.01)
*C07D 403/14* (2006.01)
*C07D 251/24* (2006.01)
*C07D 487/04* (2006.01)
*C09K 11/06* (2006.01)
*C07D 209/88* (2006.01)

| | | |
|---|---|---|
| C07D 265/38 | (2006.01) | |
| C07D 279/28 | (2006.01) | |
| C07D 241/48 | (2006.01) | |
| C07D 403/10 | (2006.01) | |
| C07D 417/14 | (2006.01) | |

(52) U.S. Cl.
CPC ......... *C07D 251/24* (2013.01); *C07D 265/38* (2013.01); *C07D 279/28* (2013.01); *C07D 403/10* (2013.01); *C07D 403/14* (2013.01); *C07D 413/14* (2013.01); *C07D 417/14* (2013.01); *C07D 487/04* (2013.01); *C09K 11/06* (2013.01); *H01L 51/0059* (2013.01); *H01L 51/0067* (2013.01); *H01L 51/50* (2013.01); *H01L 51/5012* (2013.01); *H01L 51/5056* (2013.01); *H01L 51/5072* (2013.01); *H01L 51/5088* (2013.01)

(56) References Cited

FOREIGN PATENT DOCUMENTS

| | | | |
|---|---|---|---|
| CN | 103012206 | A | 4/2013 |
| CN | 104245785 | A | 12/2014 |
| CN | 104277824 | A | 1/2015 |
| CN | 104716268 | A | 6/2015 |
| CN | 105602553 | A | 9/2015 |
| CN | 105418533 | A | 3/2016 |
| CN | 105418533 | A | 5/2016 |
| CN | 105602553 | A | 5/2016 |
| EP | 2 711 359 | A1 | 3/2014 |
| EP | 2722359 | A1 | 4/2014 |
| EP | 2851408 | A1 | 3/2015 |
| EP | 3112439 | * | 1/2017 |
| JP | 2013-256490 | A | 12/2013 |
| JP | 2014-043541 | A | 3/2014 |
| JP | 2014-172852 | A | 9/2014 |
| JP | 2015-065225 | A | 4/2015 |
| JP | 2015-179809 | A | 10/2015 |
| KR | 10-2013-0062895 | A | 6/2013 |
| TW | 201443028 | A | 11/2014 |
| TW | 201542506 | A | 11/2015 |
| WO | 2011070963 | A1 | 6/2011 |
| WO | 2013/085285 | A1 | 6/2013 |
| WO | 2013081088 | A1 | 6/2013 |
| WO | 2014194971 | A1 | 12/2014 |
| WO | 2015022835 | A1 | 2/2015 |
| WO | 2015080183 | A1 | 6/2015 |
| WO | 2015/129715 | A1 | 9/2015 |
| WO | 2015133353 | A1 | 9/2015 |
| WO | 2015135625 | A1 | 9/2015 |
| WO | 2015135626 | A1 | 9/2015 |
| WO | 2016/174377 | A1 | 11/2016 |
| WO | 2015/129715 | A1 | 3/2017 |

OTHER PUBLICATIONS

Ishow et al., Multicolor Emission of Small Molecule-Based Amorphous Thin Films and Nanoparticles with a Single Excitation Wavelength, Chem. Mater., vol. 20, No. 21, pp. 6597-6599, (2008).*
Thomas et al., Light-Emitting Carbazole Derivatives: Potential Electroluminescent Materials, J. Am. Soc.,vol. 123, No. 38, pp. 9404-9411 (2001).*
Nakanotani, H., et al., "High-efficiency organic light-emitting diodes with fluorescent emitters" Nature communications, vol. 5, Article No. 4016, pp. 1-26 (May 30, 2014).
Yue-Qin, P., et al., "Synthesis and Photovoltaic Properties od D-Pie-A Type Conjugated Polymers," Journal of Functional Polymers, vol. 27 , No. 2, pp. 129-137 (Jun. 2014) (English Abstract).
M Kim et. al., "Simultaneous improvement of emission color, singlet-triplet energy gap, and quantum efficiency of blue thermally activated delayed fluorescent emitters using a 1-carbazolylcarbazole based donor", Chemical Communications, vol. 52, Jul. 12, 2015, pp. 10032-10035.
W-L Tsai et. al., "A versatile thermally activated delayed fluorescence emitter for both highly efficient doped and non-doped organic light emitting devices", Chemical Communications, vol. 51, Jul. 20, 2015, pp. 13662-13665.
D. R. Lee et. al., "Design Strategy for 25% External Quantum Efficiency in Green and Blue Thermally Activated Delayed Fluorescent Devices", Advanced Materials, vol. 27, Aug. 26, 2015, pp. 5861-5867.
CN Office Action in application No. 201510957493.2 dated Jul. 17, 2019.
Andreas Kretzschmar et. al., "Development of Thermally Activated Delayed Fluorescence Materials with Shortened Emissive Lifetimes", The Journal of Organic Chemistry, vol. 80, Aug. 20, 2015, pp. 9126-9131.
CN Office Action in application No. 2018-524282 dated May 28, 2019.

* cited by examiner

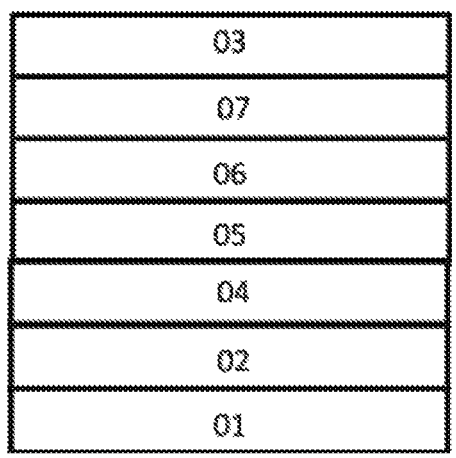

THERMALLY ACTIVATED DELAYED FLUORESCENCE MATERIAL AND APPLICATION THEREOF IN ORGANIC ELECTROLUMINESCENCE DEVICE

TECHNICAL FIELD

The present invention belongs to the field of materials, and particularly relates to a thermally activated delayed fluorescence material and application thereof in an organic electroluminescence device.

BACKGROUND ART

In the electroluminescence process of an organic electroluminescence device, luminescence occurs mainly due to the electronic transition of an organic luminescent material from an excited state to a ground state. At room temperature, luminescence generated by the electronic transition from a triplet excited state back to the ground state is extremely weak, most of the energy is lost in the form of heat, and luminescence is mainly generated by the electronic transition from a singlet excitation state to the ground state, and is called electroluminescence. Since the probability of the triplet excited state is three times that of the singlet excitation state, the equivalent of 75% of the energy is not used for luminescence. Making full use of the energy will effectively improve the luminescence efficiency of the organic electroluminescence device.

In order to make full use of the energy of the triplet excited state of a host material of a luminescent layer, various methods have been proposed. For example, by researching and developing an efficient phosphorescence doping dye and doping the phosphorescence doping dye into the host material, the triplet energy of the host material can be effectively transmitted to the phosphorescence doping dye, and then the phosphorescence doping dye generates phosphorescence, thereby allowing the energy of the triplet excited state of the host material of the luminescent layer to be effectively used. The organic electroluminescence device obtained by this method has high efficiency, but material synthesis requires precious metals such as ruthenium and platinum which are expensive. Another method is to utilize the intersystem crossing property of lanthanide compounds, namely intramolecular energy transfer, to transfer the triplet energy of the host material of the luminescent layer to the 4f energy level of lanthanide metal ions, and then luminescence and the like are achieved, but current devices are inefficient.

Thermally activated delayed fluorescence (TADF) is a quite popular scheme utilizing triplet exciton energy at present. For example, Adachi reported in his article a thermally activated delayed fluorescence material which has a small difference ($\Delta E_{ST}$) between the triplet energy level ($T_1$) and the singlet energy level ($S_1$), in this way, triplet energy can be transmitted to the singlet energy level, and light is emitted through fluorescent radiation. Patent CN 102709485 A mentions that device efficiency is improved by doping a fluorescent dye in a thermal delay fluorescent host. In order to further improve energy transmission recombination efficiency, in the article "High-efficiency organic light-emitting diodes with fluorescent emitters" by Adachi et al. in Nature communications 2014, a wide-band-gap host doped TADF material is proposed as an auxiliary dye solution. However, in the process of charge recombination, part of the energy is directly compounded on a host, the host transmits the singlet energy to a dye, and the other part is compounded on an auxiliary dye. The structure reported in the article can not fully and effectively utilize the energy directly compounded on the host. At the same time, an ordinary host material is used, a band gap is wide, and required driving voltage is high.

However, the current TADF material has a short lifetime, and one of the reasons is that the lifetime of the triplet state is too long, and exciton quenching can be caused easily due to processes such as TPA. Therefore, the lifetime of a TADF device can be effectively increased by reducing the lifetime of triplet excitons.

Technical Problems

The technical problem to be solved by the present invention is that a TADF material in the prior art has a short lifetime.

Technical Solution

In order to solve the above technical problem, the present invention provides a novel TADF material. By introducing heavy atoms such as bromine or iodine into original TADF molecules, reverse intersystem crossing and intersystem crossing of the TADF material can be increased through the heavy atom effect, so that the lifetime of triplet excitons can be reduced, and ultimately the lifetime of a device can be increased.

The thermally activated delayed fluorescence material provided by the present invention is a compound having the general structure of Formula I or Formula II:

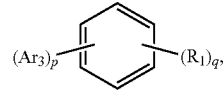

Formula I

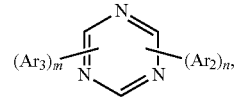

Formula II

In Formula I and Formula II, $R_1$ is a cyano, p is 1, 2 or 3, q is 1, 2 or 3, m is 1 or 2, n is 1 or 2,
$Ar_1$ is a phenyl substituted with one or more groups selected from $C_{1-6}$ alkyl, methoxy, ethoxy, or phenyl,
$Ar_2$ and $Ar_3$ are selected from the following groups:

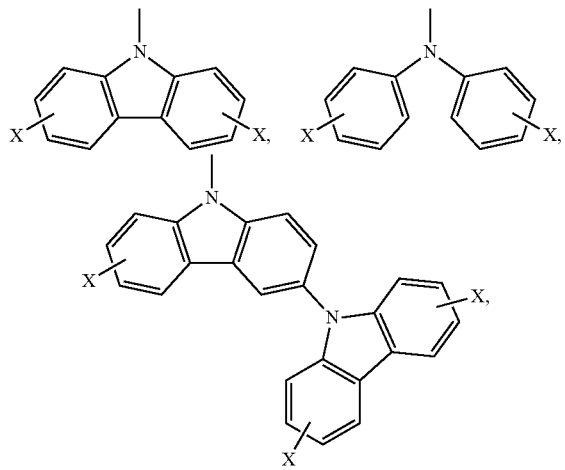

-continued
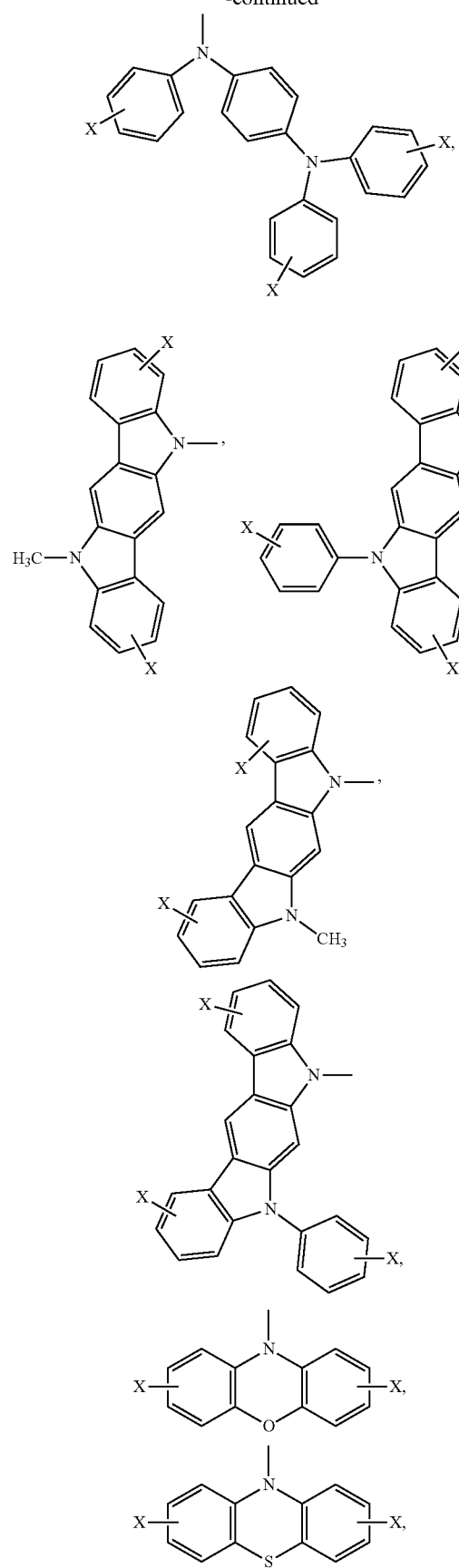
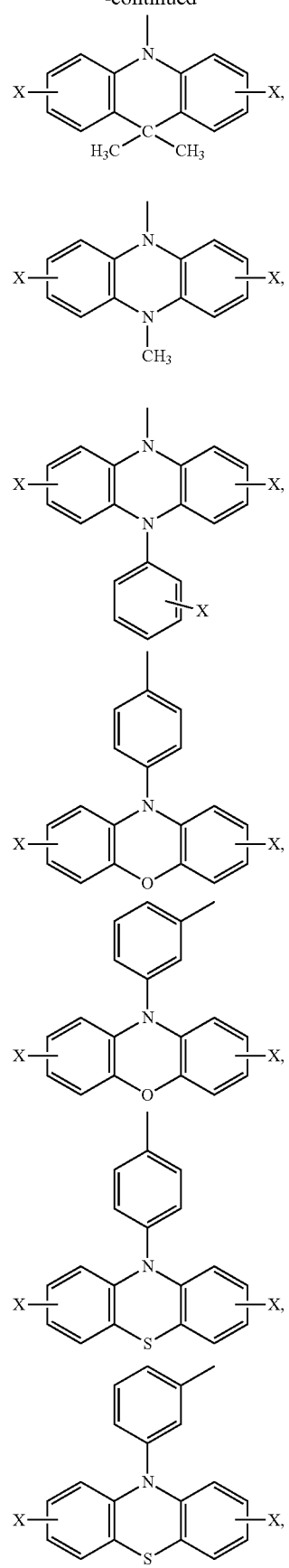

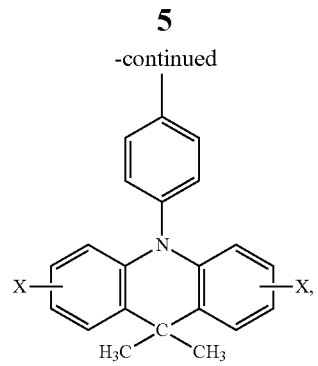
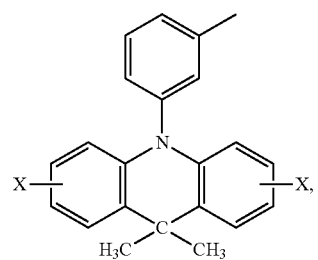
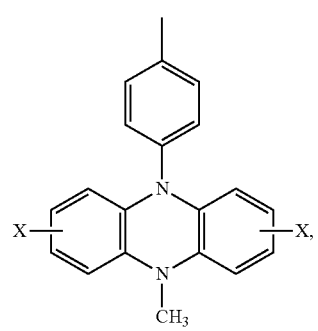
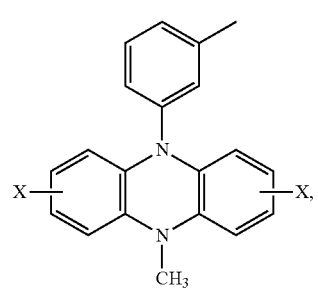
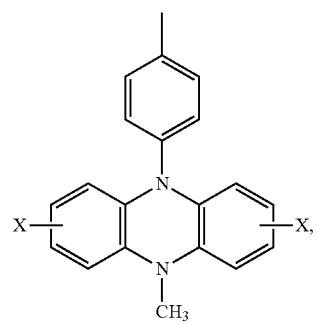
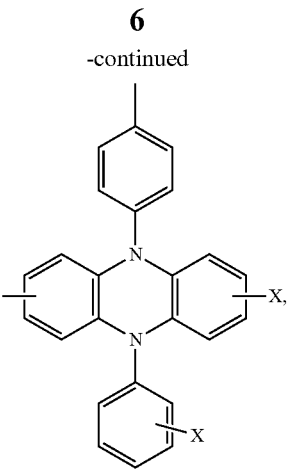
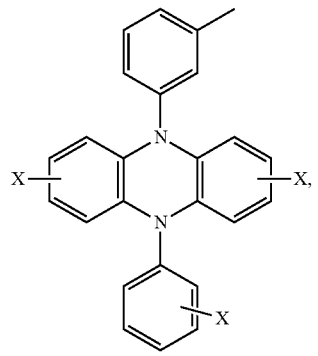
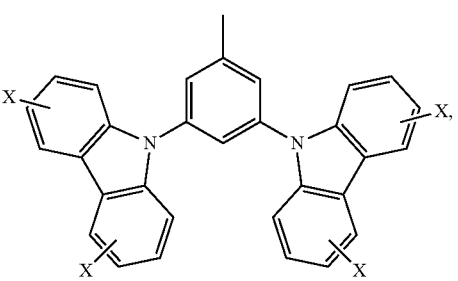
and X is bromine or iodine.
Preferably, the thermally activated delayed fluorescence material is a compound having the following structure:
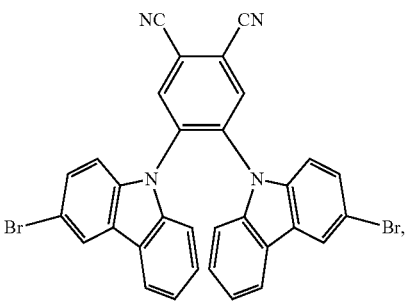
1-1

1-2
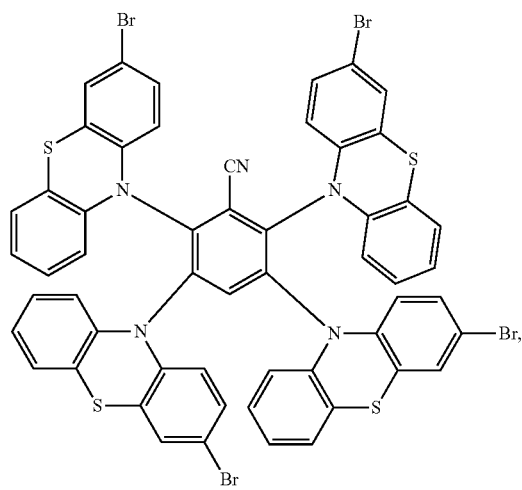
1-5
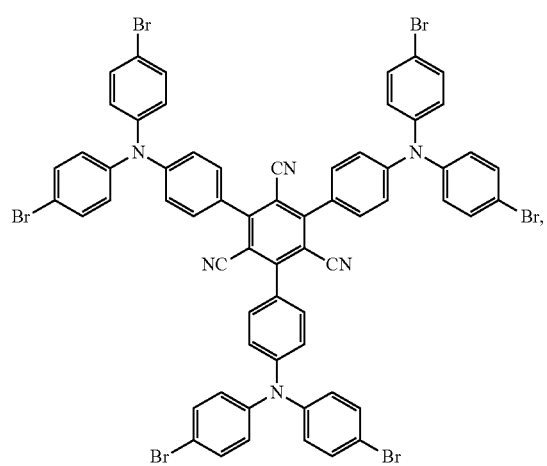
1-3
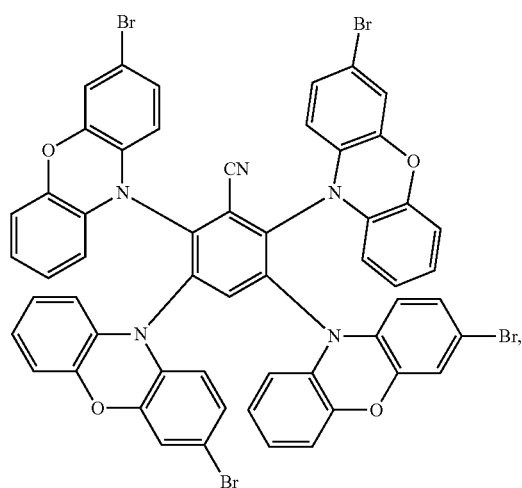
2-1
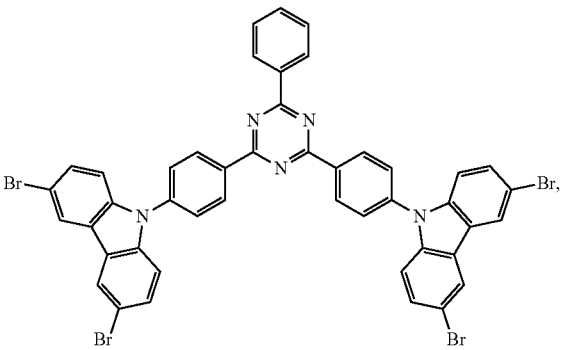
1-4
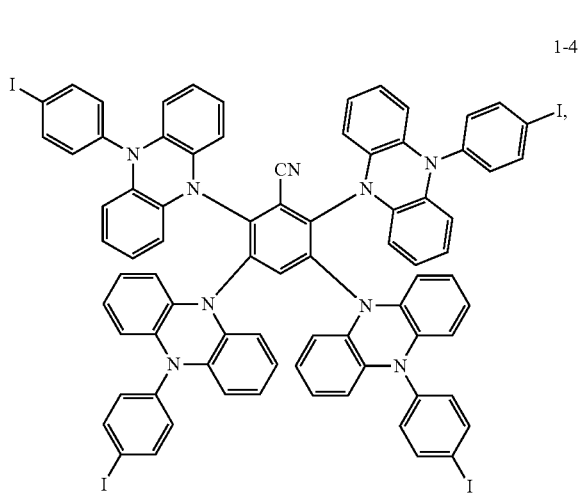
2-2
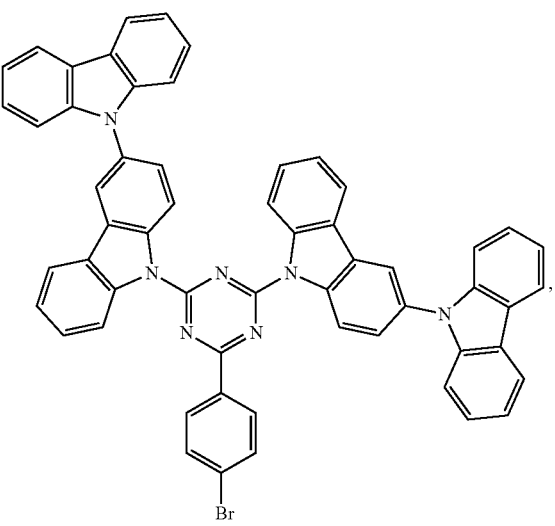

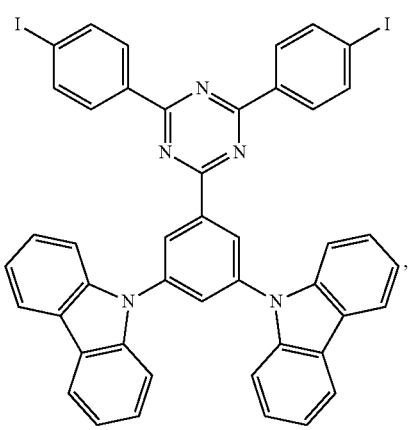

2-3

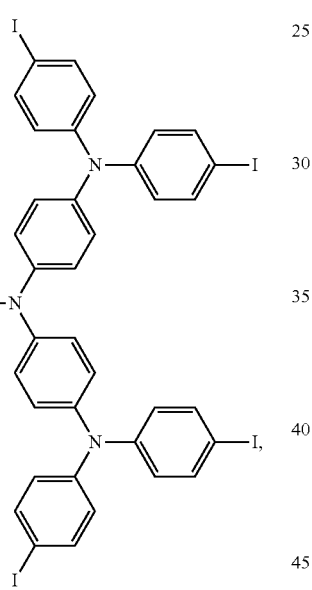

2-4

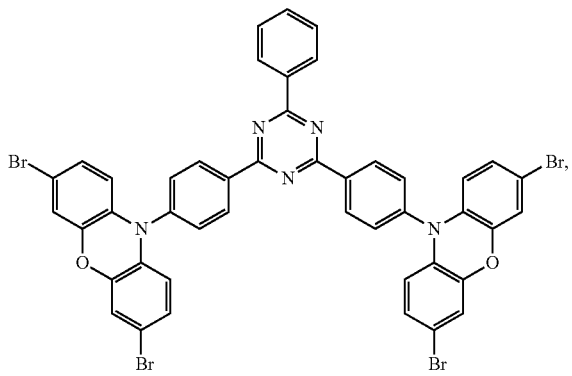

2-5

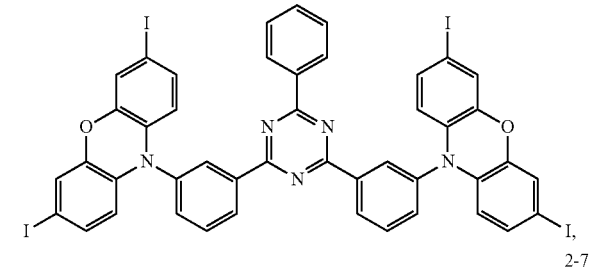

2-6

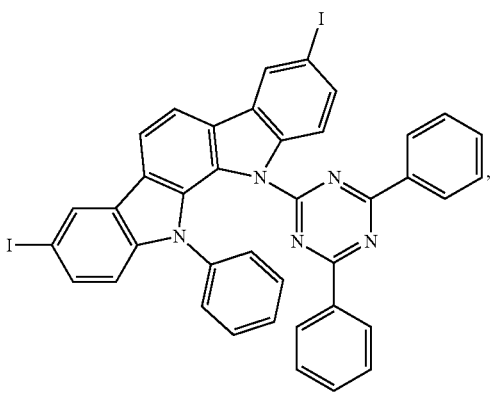

2-7

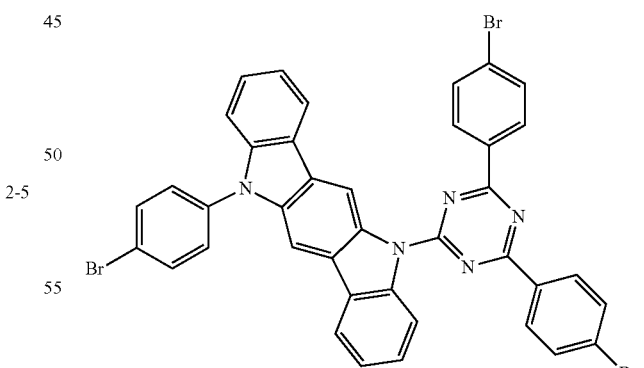

2-8

2-9

The present invention also provides application of the thermally activated delayed fluorescence material as a host material or a luminescent dye of a luminescent layer of an organic electroluminescence device.

The present invention further provides an organic electroluminescence device, comprising a luminescent layer, the luminescent layer comprises a host material and a luminescent dye doped in the host material, and the luminescent dye is the above thermally activated delayed fluorescence material. Preferably, the luminescent dye accounts for 0.5 wt %-10 wt % of the luminescent layer, and more preferably 5 wt %.

As a preferred technical solution, the organic electroluminescence device described above comprises an anode, a hole transport layer, a luminescent layer, an electron transport layer, and a cathode, which are successively deposited on a substrate and are laminated.

Preferably, a hole injection layer is further disposed between the anode and the hole transport layer.

The present invention further provides an organic electroluminescence device, comprising a luminescent layer, the luminescent layer comprises a host material and a luminescent dye doped in the host material, and the host material is the above thermally activated delayed fluorescence material.

Preferably, the luminescent dye accounts for 1 wt %-10 wt % of the luminescent layer.

Advantageous Effects

According to the TADF material provided by the invention, by introducing heavy atoms such as bromine or iodine into molecules, the lifetime of the triplet state of the TADF material is reduced, and efficiency roll-off is reduced, thereby increasing the lifetime of the organic electroluminescence device.

BRIEF DESCRIPTION OF THE DRAWINGS

FIG. 1 is the schematic diagram of the structure of an organic electroluminescence device of the present invention.

PREFERRED EMBODIMENTS OF THE INVENTION

The present invention will be further illustrated below by referring to the drawings and the special examples, to enable a person skilled in the art to better understand and implement the present invention, but the examples are not taken as limiting the present invention.

A thermally activated delayed fluorescence material provided in the invention is a compound having the general structure of Formula I or Formula II:

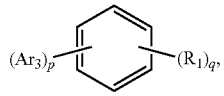

Formula I

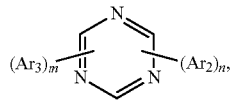

Formula II

In Formula I and Formula II, $R_1$ is a cyano, p is 1, 2 or 3, q is 1, 2 or 3, m is 1 or 2, n is 1 or 2, $Ar_1$ is a phenyl substituted with one or more groups selected from $C_{1-6}$ alkyl, methoxy, ethoxy, or phenyl, $Ar_2$ and $Ar_3$ are selected from the following groups:

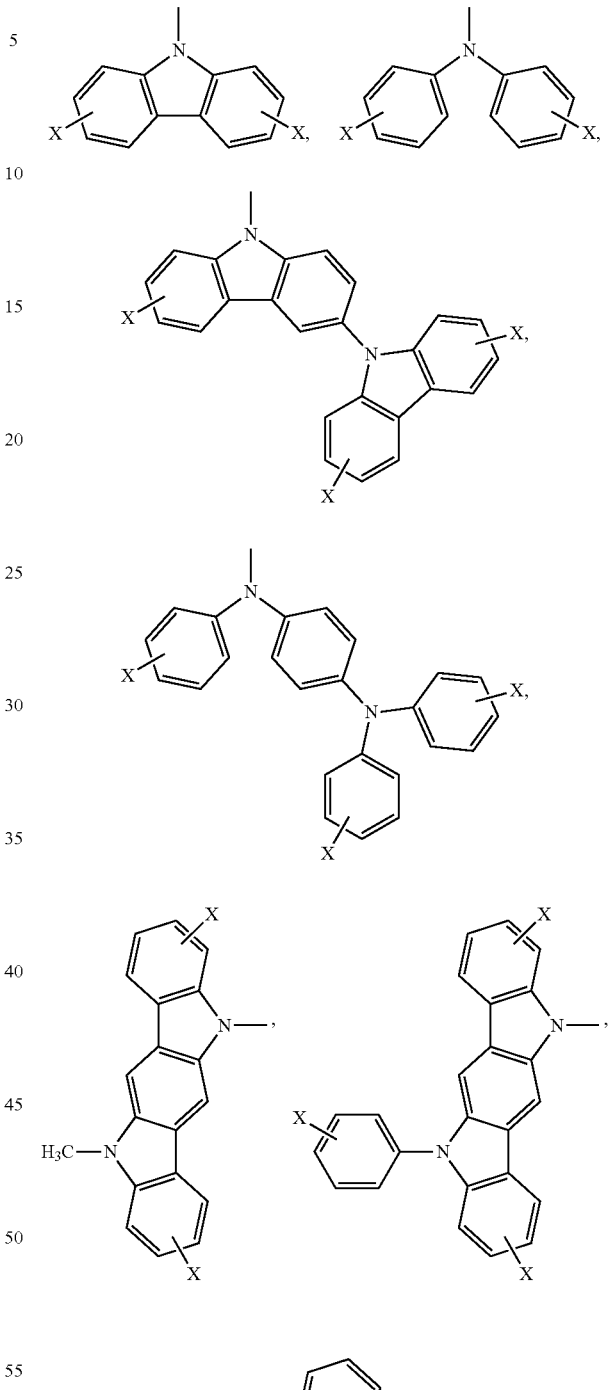

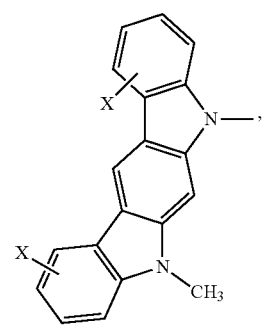

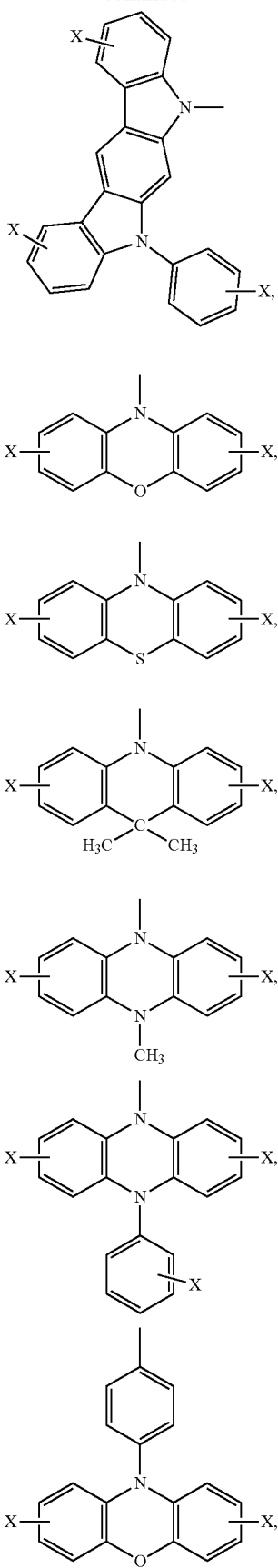
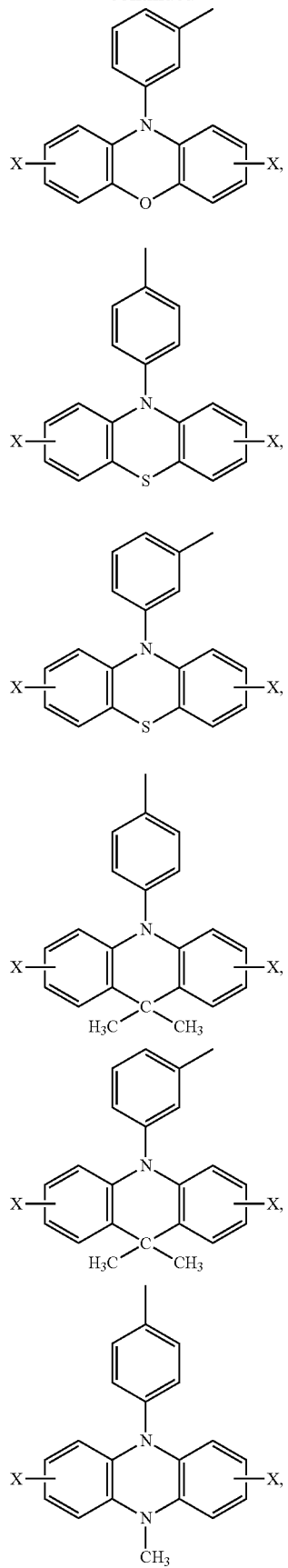

-continued

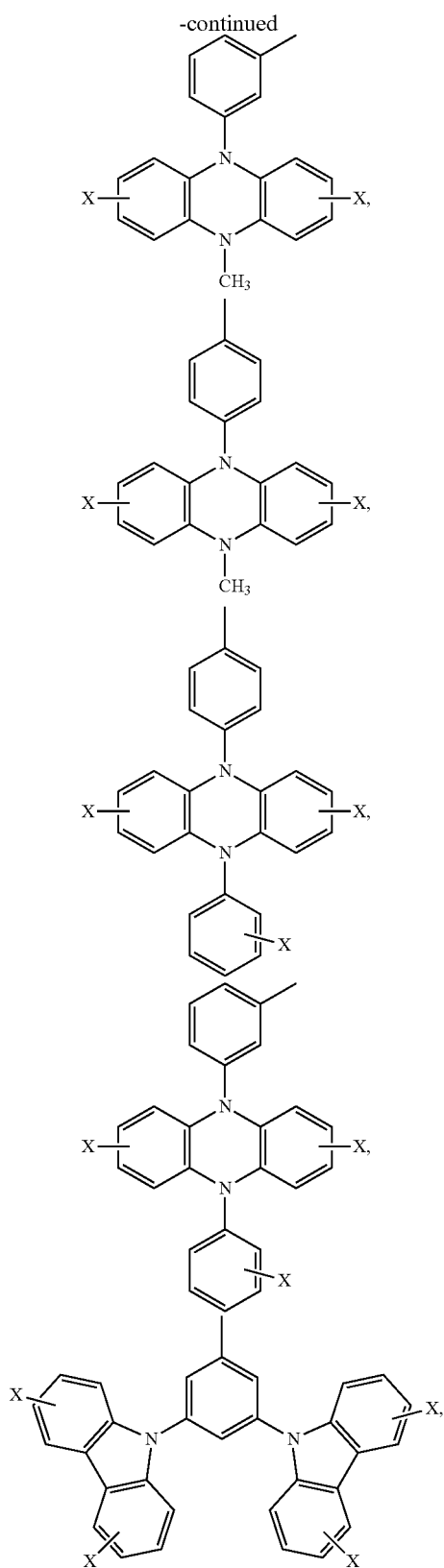

and X is bromine or iodine.

According to the thermally activated delayed fluorescence material, by introducing heavy atoms such as bromine or iodine into original TADF molecules, reverse intersystem crossing and intersystem crossing of the TADF material can be increased through the heavy atom effect, so that the lifetime of triplet excitons can be reduced, and ultimately the lifetime of a device can be increased.

Specifically, the thermally activated delayed fluorescence material of the present invention is compounds having the following structures, and properties and preparation methods of the compounds are as follows:

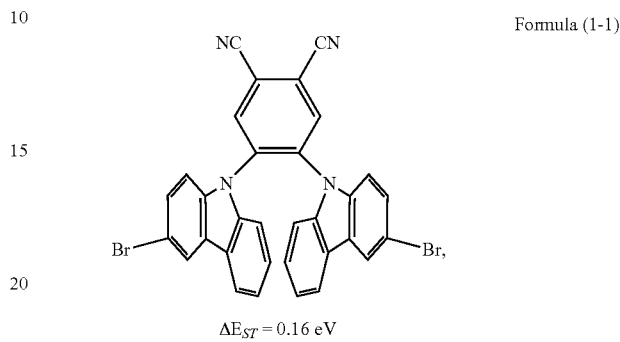

Formula (1-1)

$\Delta E_{ST} = 0.16$ eV

Preparation Method:

Synthesis of the compound having the structure represented by Formula (1-1): in the nitrogen range, 3-bromocarbazole (5 mmol) is dissolved in 2 mL of anhydrous THF, then sodium hydride (5 mmol) is added, and the mixture is stirred at room temperature for 30 minutes; subsequently, 1,2-dicyano-4,5-difluorobenzene (1 mmol) is added to a reaction flask and stirring is continued for 1 hour; finally, 2 mL of cold water is added to the mixture to quench the reaction. After the mixture is cooled to room temperature, a product of Formula (1-1) is purified by vacuum filtration followed by column chromatography, and the product is dried in vacuum. Yield: 75%.

Molecular weight obtained through mass spectrometry: 615.97.

Relative molecular mass percentage of each element obtained through elemental analysis: C: 62.36; H: 2.62; N: 9.09; Br: 25.93.

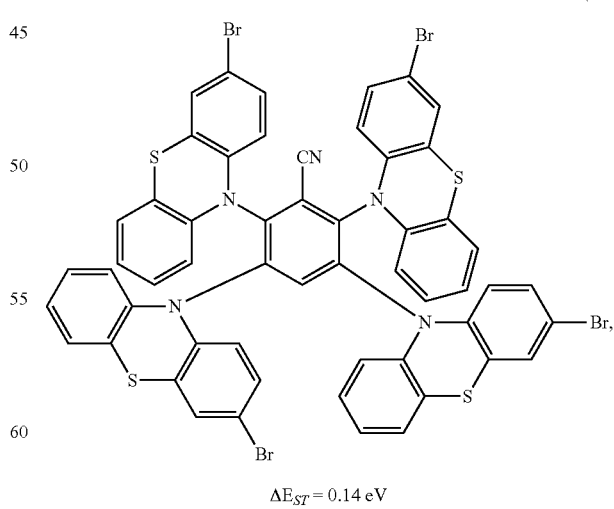

Formula (1-2)

$\Delta E_{ST} = 0.14$ eV

Preparation Method:

Synthesis of the compound having the structure represented by Formula (1-2): in the nitrogen range, 3-bromophenothiazine (10 mmol) is dissolved in 4 mL of anhydrous THF, then sodium hydride (10 mmol) is added, and the mixture is stirred at room temperature for 30 minutes; subsequently, 2,3,5,6-tetrafluoro nitrile benzene (1 mmol) is added to a reaction flask and stirring is continued for 1 hour; finally, 2 mL of cold water is added to the mixture to quench the reaction. After the mixture is cooled to room temperature, a product of Formula (1-2) is purified by vacuum filtration followed by column chromatography, and the product is dried in vacuum. Yield: 62%.

Molecular weight obtained through mass spectrometry: 1206.80.

Relative molecular mass percentage of each element obtained through elemental analysis: C: 54.70; H: 2.42; N: 5.80; S: 10.62; Br: 26.46.

Formula (1-3)

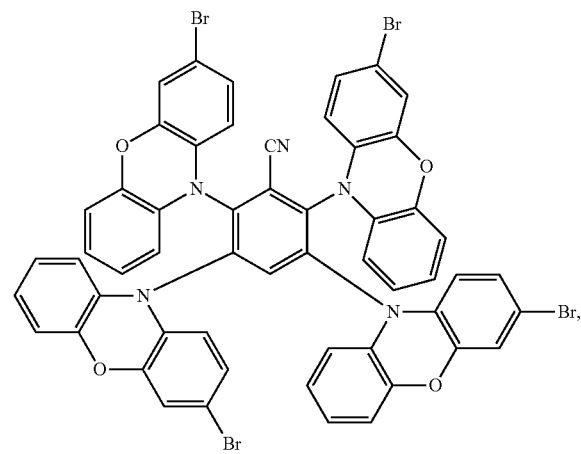

$\Delta E_{ST} = 0.13$ eV

Preparation Method:

Synthesis of the compound having the structure represented by Formula (1-3): the reactant 3-bromophenothiazine is replaced with 3-bromophenoxazine, the compound having the structure represented by Formula (1-3) is obtained by a synthesis method which is the same as that of Formula (1-2), and yield is 59%.

Molecular weight obtained through mass spectrometry: 1142.89.

Relative molecular mass percentage of each element obtained through elemental analysis: C: 57.77; H: 2.56; N: 6.12; O: 5.60; Br: 27.95.

Formula (1-4)

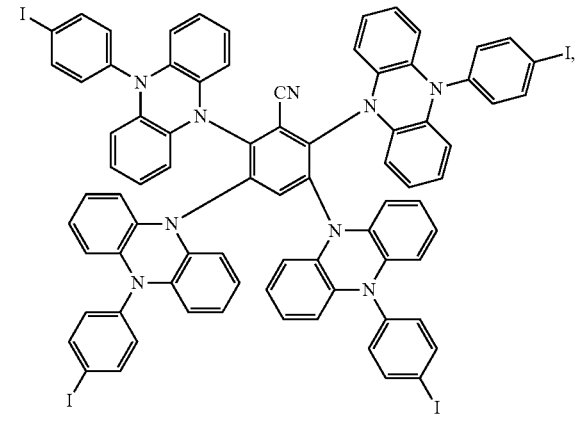

$\Delta E_{ST} = 0.13$ eV

Preparation Method:

Synthesis of the compound having the structure represented by Formula (1-4): the reactant 3-bromophenothiazine is replaced with 9-p-iodobenzene phenazine, the compound having the structure represented by Formula (1-4) is obtained by a synthesis method which is the same as that of Formula (1-2), and yield is 55%.

Molecular weight obtained through mass spectrometry: 1631.03.

Relative molecular mass percentage of each element obtained through elemental analysis: C: 58.14; H: 3.03; N: 7.72; I: 31.11.

Formula (1-5)

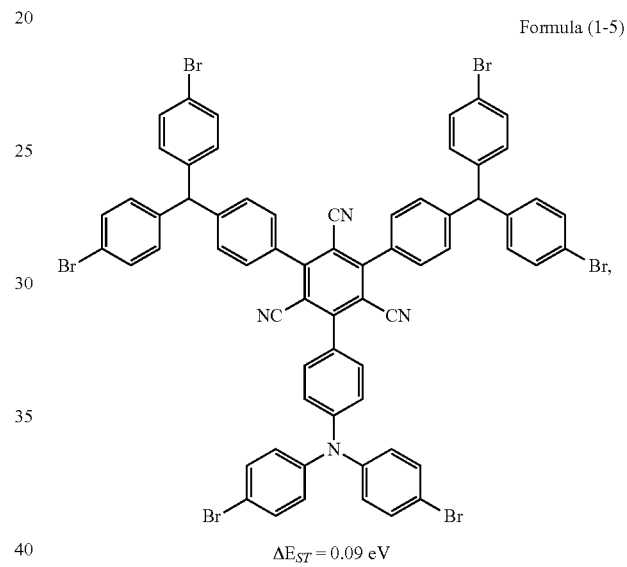

$\Delta E_{ST} = 0.09$ eV

Preparation Method:

Synthesis of the compound having the structure represented by Formula (1-5): in the nitrogen range, (1,1'-p-dibromobenzene) p-aminobenzene (15 mmol) is dissolved in 6 mL of anhydrous THF, then sodium hydride (15 mmol) is added, and the mixture is stirred at room temperature for 30 minutes; subsequently, 2,4,6-tetrafluoro-1,3,5-tricyanobenzene (1 mmol) is added to a reaction flask and stirring is continued for 1 hour; finally, 2 mL of cold water is added to the mixture to quench the reaction. After the mixture is cooled to room temperature, a product of Formula (1-5) is purified by vacuum filtration followed by column chromatography, and the product is dried in vacuum. Yield: 31%.

Molecular weight obtained through mass spectrometry: 1355.80.

Relative molecular mass percentage of each element obtained through elemental analysis: C: 55.78; H: 2.68; N: 6.20; Br: 35.34.

Formula (2-1)

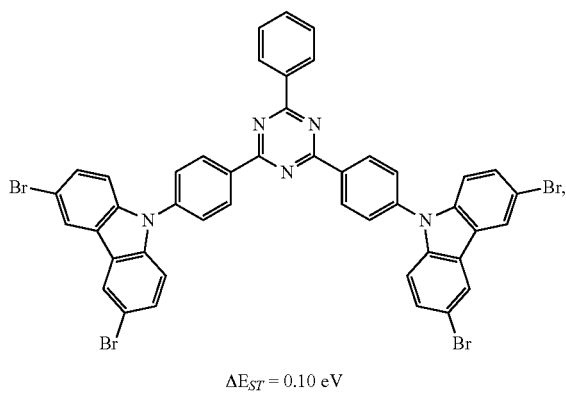

$\Delta E_{ST} = 0.10$ eV

Preparation Method:

Synthesis of the compound having the structure represented by Formula (2-1): in the nitrogen range, 3,6-dibromocarbazolylbenzene (10 mmol) is dissolved in 4 mL of anhydrous THF, then sodium hydride (15 mmol) is added, and the mixture is stirred at room temperature for 30 minutes; subsequently, 1-phenyl-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-1) is purified by vacuum filtration followed by column chromatography, and the product is dried in vacuum. Yield: 49%.

Molecular weight obtained through mass spectrometry: 955.33.

Relative molecular mass percentage of each element obtained through elemental analysis: C: 56.58; H: 2.64; N: 7.33; Br: 33.46.

Formula (2-2)

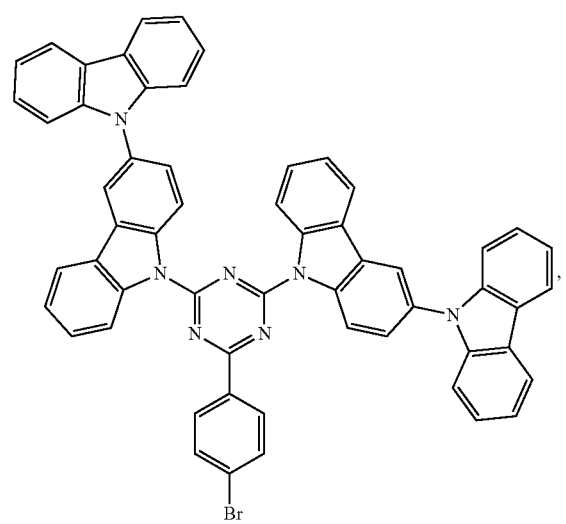

$\Delta E_{ST} = 0.15$ eV

Preparation Method:

Synthesis of the compound having the structure represented by Formula (2-2): in the nitrogen range, p-bromobenzene (5 mmol) is dissolved in 4 mL of anhydrous THF, then sodium hydride (5 mmol) is added, and the mixture is stirred at room temperature for 30 minutes; subsequently, 2,4-bis(3-bicarbazole)-6-fluoro-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-2) is purified by vacuum filtration followed by column chromatography, and the product is dried in vacuum. Yield: 53%.

Molecular weight obtained through mass spectrometry: 895.21.

Relative molecular mass percentage of each element obtained through elemental analysis: C: 76.34; H: 3.82; N: 10.93; Br: 8.91.

Formula (2-3)

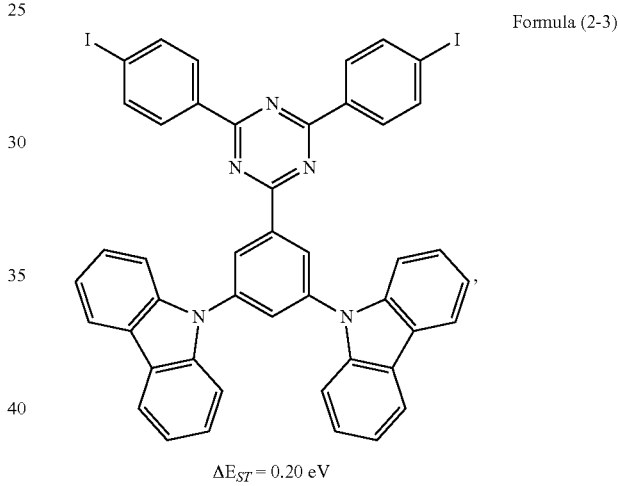

$\Delta E_{ST} = 0.20$ eV

Preparation Method:

Synthesis of the compound having the structure represented by Formula (2-3): in the nitrogen range, p-iodobenzene (10 mmol) is dissolved in 4 mL of anhydrous THF, then sodium hydride (10 mmol) is added, and the mixture is stirred at room temperature for 30 minutes; subsequently, 2,4-bis(3-bicarbazole)-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-3) is purified by vacuum filtration followed by column chromatography, and the product is dried in vacuum. Yield: 53%.

Molecular weight obtained through mass spectrometry: 891.04.

Relative molecular mass percentage of each element obtained through elemental analysis: C: 60.62; H: 3.05; N: 7.86; I: 28.47.

Formula (2-4)

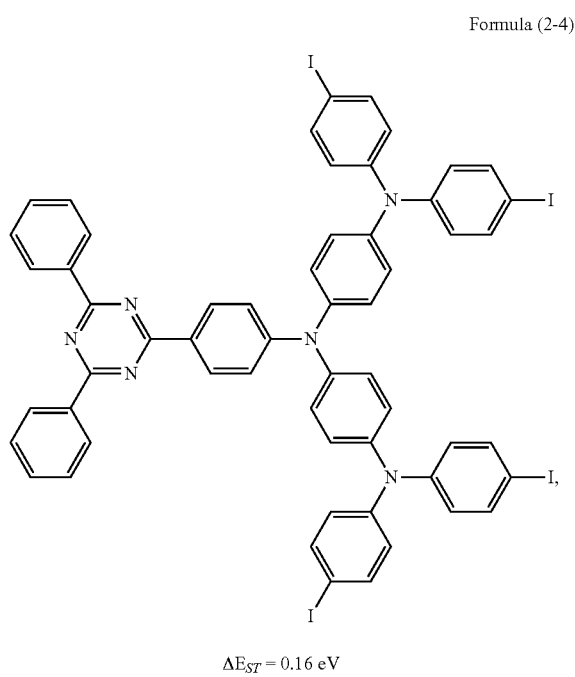 [SMILES: Ic1ccc(N(c2ccc(I)cc2)c2ccc(N(c3ccc(-c4nc(-c5ccccc5)nc(-c5ccccc5)n4)cc3)c3ccc(N(c4ccc(I)cc4)c4ccc(I)cc4)cc3)cc2)cc1]

ΔE$_{ST}$ = 0.16 eV

Preparation Method:

Synthesis of the compound having the structure represented by Formula (2-4): in the nitrogen range, p-diiodobenzene-4,4'-diaminobenzenes (5 mmol) is dissolved in 4 mL of anhydrous THF, then sodium hydride (5 mmol) is added, and the mixture is stirred at room temperature for 30 minutes; subsequently, 4-fluoro-2,6-phenyl-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-4) is purified by vacuum filtration followed by column chromatography, and the product is dried in vacuum. Yield: 40%.

Molecular weight obtained through mass spectrometry: 1313.93.

Relative molecular mass percentage of each element obtained through elemental analysis: C: 52.08; H: 2.91; N: 6.39; I: 38.61.

Formula (2-5)

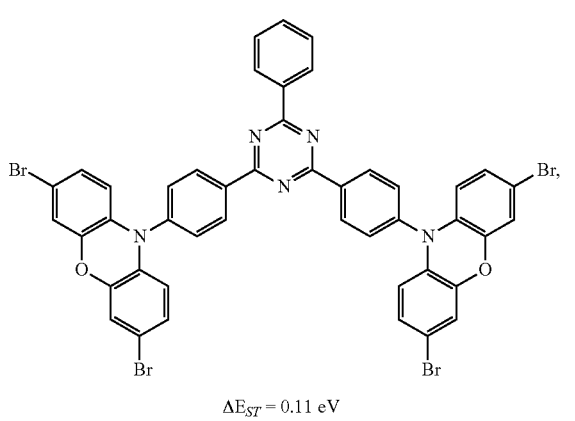

ΔE$_{ST}$ = 0.11 eV

Preparation Method:

Synthesis of the compound having the structure represented by Formula (2-5): the reactant 3,6-dibromocarbazolylbenzene is replaced with 3,7-dibromophenoxazinebenzene, the compound having the structure represented by Formula (2-5) is obtained by a synthesis method which is the same as that of Formula (2-1), and yield is 61%.

Molecular weight obtained through mass spectrometry: 986.87.

Relative molecular mass percentage of each element obtained through elemental analysis: C: 54.74; H: 2.55; N: 7.09; O: 3.24; Br: 32.37.

Formula (2-6)

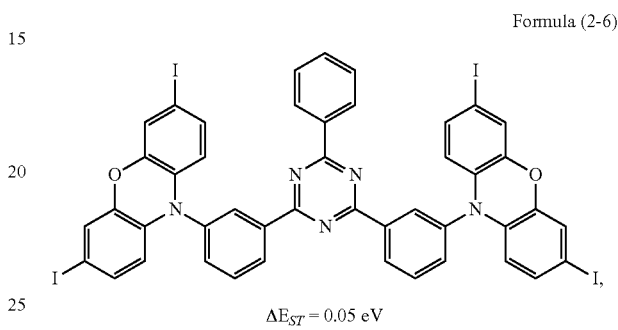

ΔE$_{ST}$ = 0.05 eV

Preparation Method:

Synthesis of the compound having the structure represented by Formula (2-6): the reactant 3,6-dibromocarbazolylbenzene is replaced with 3,7-dibromophenoxazine-m-benzene, the compound having the structure represented by Formula (2-6) is obtained by a synthesis method which is the same as that of Formula (2-1), and yield is 61%.

Molecular weight obtained through mass spectrometry: 1174.82.

Relative molecular mass percentage of each element obtained through elemental analysis: C: 45.99; H: 2.14; N: 5.96; O: 2.72; I: 43.19.

Formula (2-7)

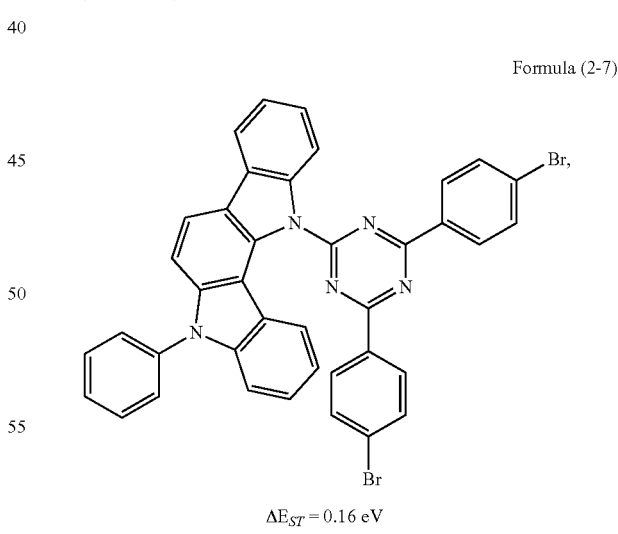

ΔE$_{ST}$ = 0.16 eV

Preparation Method:

Synthesis of the compound having the structure represented by Formula (2-7): in the nitrogen range, dibromobenzene (10 mmol) is dissolved in 4 mL of anhydrous THF, then sodium hydride (10 mmol) is added, and the mixture is stirred at room temperature for 30 minutes; subsequently, 2,4-difluoro-6-(11-phenyl-11,12-dihydroindolo[3,2b]carbazolyl)-2,6-phenyl-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-7) is purified by vacuum filtration followed by column chromatography, and the product is dried in vacuum. Yield: 34%.

Molecular weight obtained through mass spectrometry: 721.03.

Relative molecular mass percentage of each element obtained through elemental analysis: C: 64.93; H: 3.21; N: 9.71; Br: 22.15.

Formula (2-8)

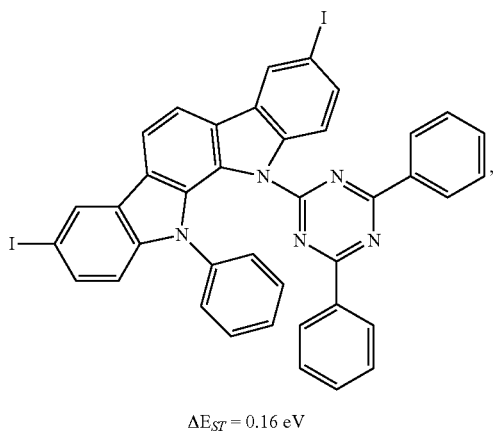

$\Delta E_{ST} = 0.16$ eV

Preparation Method:

Synthesis of the compound having the structure represented by Formula (2-8): in the nitrogen range, 6-phenyl-2,9-diiodo-indolo[2,3a]carbazole (10 mmol) is dissolved in 4 mL of anhydrous THF, then sodium hydride (10 mmol) is added, and the mixture is stirred at room temperature for 30 minutes; subsequently, 6-fluoro-2,4-diphenyl-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-8) is purified by vacuum filtration followed by column chromatography, and the product is dried in vacuum. Yield: 31%.

Molecular weight obtained through mass spectrometry: 815.44.

Relative molecular mass percentage of each element obtained through elemental analysis: C: 57.44; H: 2.84; N: 8.59; I: 31.13.

Formula (2-9)

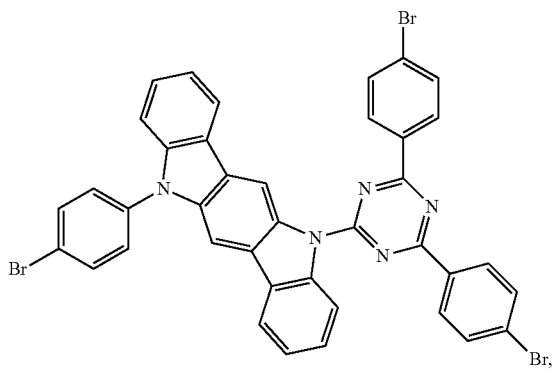

$\Delta E_{ST} = 0.17$ eV

Preparation Method:

Synthesis of the compound having the structure represented by Formula (2-9): in the nitrogen range, 11-p-bromophenyl-indolo[2,3a]carbazole (7 mmol) is dissolved in 4 mL of anhydrous THF, then sodium hydride (10 mmol) is added, and the mixture is stirred at room temperature for 30 minutes; subsequently, 6-fluoro-2,4-p-dibromophenyl-1,3,5-triazine (1 mmol) is added to a reaction flask and stirring is continued for 1 hour; finally, 2 mL of cold water is added to the mixture to quench the reaction. After the mixture is cooled to room temperature, a product of Formula (2-9) is purified by vacuum filtration followed by column chromatography, and the product is dried in vacuum. Yield: 36%.

Molecular weight obtained through mass spectrometry: 800.34.

Relative molecular mass percentage of each element obtained through elemental analysis: C: 58.53; H: 2.77; N: 8.75; Br: 29.95.

The thermally activated delayed fluorescence material of the present invention can be used as a luminescent dye for a luminescent layer of an organic electroluminescence device.

As shown by FIG. 1, the organic electroluminescence device of the present invention comprises an anode 02, a hole injection layer 04, a hole transport layer 05, a luminescent layer 06, an electron transport layer 07 and a cathode 03, which are successively deposited on a substrate 01 and are laminated.

The material of the luminescent layer 06 comprises a host material and a luminescent dye doped in the host material, and the luminescent material is a compound having the structure of Formula I or Formula II.

The embodiments of the organic luminescence display device of the present invention: the anode 02 may employ an inorganic material or an organic conductive polymer. The inorganic material may generally employ metal oxides such as indium tin oxide (ITO), zinc oxide (ZnO), and indium zinc oxide (IZO) or metals of high work functions such as gold, copper and silver, preferably ITO. The organic conductive polymer is preferably one of polythiophene/polyvinyl sodium benzenesulfonate (hereafter referred to as simply PEDOT/PSS) and polyaniline (hereafter referred to as simply PANI).

The cathode 03 generally employs metals of low work function such as lithium, magnesium, calcium, strontium, aluminum and indium or their alloys with copper, gold or silver, or an electrode layer that is formed by the alternating of a metal and a metal fluoride. In the present invention the cathode is preferably laminated LiF layer and Al layer (the LiF layer is on the outer side).

The material of the hole transport layer 05 may be selected from lower molecular weight materials of the arylamine type and the branched polymer type, preferably NPB.

The material of the electron transport layer 07 may employ an organic metal complex (such as $Alq_3$, $Gaq_3$, BAlq or Ga (Saph-q)) or other materials that are commonly used for electron transport layer, such as aromatic condensed ring type (such as pentacene and perylene) or o-phenanthroline type (such as Bphen and BCP) compounds.

The organic electroluminescence device of the present invention may also be provided with the hole injection layer 04 between the anode 02 and the hole transport layer 05. The material of the hole injection layer 04 may employ, for example, 4,4',4"-tris(3-methylphenylaniline)triphenylamine doped F4TCNQ or copper phthalocyanine (CuPc), or may be a metal oxide, such as molybdenum oxide and rhenium oxide.

The thicknesses of the layers may employ the conventional thicknesses of the layers in the art.

The present invention further provides a preparation method of the organic electroluminescence device, which comprises successively depositing on the substrate 01 the anode 02, the hole injection layer 04, the hole transport layer 05, the luminescent layer 06, the electron transport layer 07 and the cathode 03, which are laminated, and packaging.

The substrate may be glass or a flexible base sheet. The flexible base sheet may employ a polyester type or polyimide type compound material or a thin sheet metal. The laminating and the packaging may employ any suitable method that is known by a person skilled in the art.

Comparative Example 1

This comparative example uses ITO (indium tin oxide) as the anode; NPB as the hole injection layer; TCTA as the hole transport layer; the luminescent layer uses CBP as the host material and DSA-Ph as the luminescent dye, and the mass percentage of the luminescent dye doped in the luminescent layer is 5 wt %; Bphen as the electron transport layer; LiF (5 nm)/Al as the cathode. The structures are as follows:

ITO/NPB (40 nm)/TCTA (10 nm)/CBP: 5 wt % DSA-Ph (30 nm)/Bphen (40 nm)/LiF (5 nm)/Al

NPB

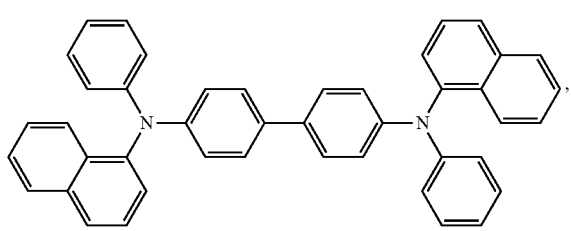

CBP

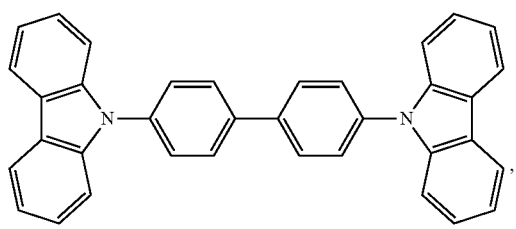

DSA-Ph

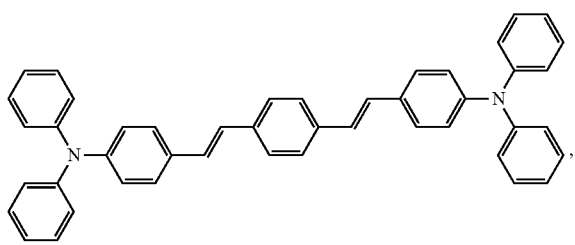

TCTA

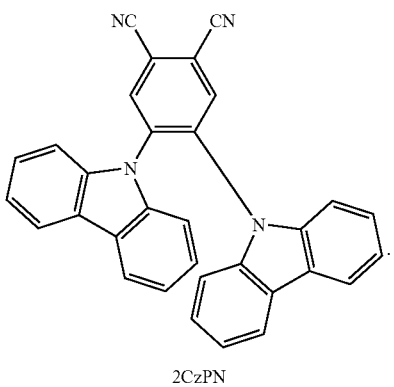 [SMILES: N#Cc1cc(-n2c3ccccc3c3ccccc32)c(-n2c3ccccc3c3ccccc32)cc1C#N]

Comparative Example 2

The structure of this Comparative Example differs from that of Comparative Example 1 only in that the luminescent dye used in the luminescent layer is 2CzPN:

ITO/NPB (40 nm)/TCTA (10 nm)/CBP: 5 wt % 2CzPN (30 nm)/Bphen (40 nm)/LiF (5 nm)/Al 2CzPN

Embodiment 1

The structure of this embodiment differs from that of Comparative Example 1 only in that the luminescent dye used in the luminescent layer is compound 1-1 of the present invention:

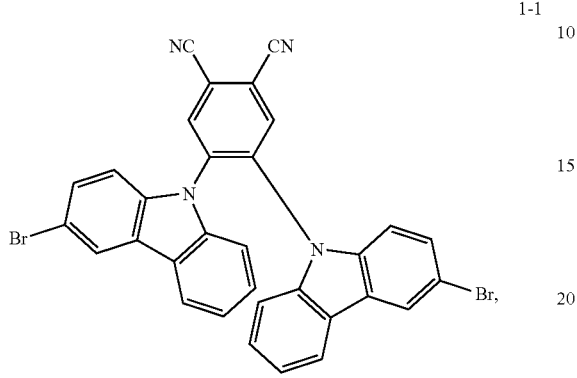

1-1

ITO/NPB (40 nm)/TCTA (10 nm)/CBP: 5 wt % compound 1-1 (30 nm)/Bphen (40 nm)/LiF (5 nm)/Al

| Serial number | Luminance cd/m² | Voltage V | Current efficiency cd/A | Lumen efficiency lm/W | x (V) | y (V) | $T_{95}$ h |
|---|---|---|---|---|---|---|---|
| Comparative Example 1 | 1000 | 6.7 | 10.2 | 4.8 | 0.16 | 0.35 | 51 |
| Comparative Example 2 | 1000 | 4.5 | 11.38 | 6.25 | 0.12 | 0.32 | 24 |
| Embodiment 1 | 1000 | 4.3 | 12.20 | 7.23 | 0.14 | 0.29 | 78 |

According to the TADF material in Embodiment 1, due to the introduction of the heavy atoms, reverse intersystem crossing and intersystem crossing of the TADF material are increased through the heavy atom effect, so that the lifetime of triplet excitons is reduced, and ultimately the lifetime of the device is increased.

Embodiments 2-5

The structures of Embodiments 2-5 differ from that of Embodiment 1 only in that the doping concentration of the luminescent dye compound 1-1 in the luminescent layer is different: ITO/NPB (40 nm)/TCTA (10 nm)/CBP: 0.5-10 wt % compound 1-1 (30 nm)/Bphen (40 nm)/LiF (5 nm)/Al Embodiments with Different Doping Concentrations

| Serial number | Doping concentration of dye wt % | Luminance cd/m² | Voltage V | Current efficiency cd/A | Lumen efficiency lm/W | x (V) | y (V) | $T_{95}$ h |
|---|---|---|---|---|---|---|---|---|
| Embodiments 1 | 5 | 1000 | 4.3 | 12.20 | 7.23 | 0.14 | 0.29 | 78 |
| Embodiments 2 | 0.5 | 1000 | 3.2 | 10.35 | 6.02 | 0.14 | 0.29 | 55 |
| Embodiments 3 | 1 | 1000 | 4.0 | 10.56 | 5.98 | 0.14 | 0.29 | 61 |
| Embodiments 4 | 3 | 1000 | 4.2 | 11.32 | 6.99 | 0.14 | 0.29 | 69 |
| Embodiments 5 | 10 | 1000 | 4.4 | 10.79 | 6.89 | 0.14 | 0.29 | 79 |

From the above table, it can be seen that the increase of the concentration of the luminescent dye causes the current efficiency of the device to increase first and then decrease. When the doping concentration is 5 wt %, the current efficiency of the device is the highest, and the voltage of the device basically does not change, but the lifetime of the device is increased as the doping concentration of the luminescent dye increases.

Embodiment 6

The OLED structure in this embodiment differs from Embodiment 1 only in that the luminescent layer is doped with a different compound having the structure of Formula I or Formula II as the luminescent dye:
ITO/NPB (40 nm)/TCTA (10 nm)/CBP: 5 wt % (compound having the structure of Formula I or Formula II) (30 nm)/Bphen (40 nm)/LiF (5 nm)/Al

| Serial number | TADF material used in luminescent layer | Luminance cd/m² | Voltage V | Current efficiency cd/A | Lumen efficiency lm/W | x (V) | y (V) | $T_{95}$ h |
|---|---|---|---|---|---|---|---|---|
| OLED1 | 1-2 | 1000 | 5.4 | 13.26 | 8.98 | 0.13 | 0.22 | 59 |
| OLED2 | 1-3 | 1000 | 4.9 | 11.38 | 6.57 | 0.15 | 0.22 | 62 |
| OLED3 | 1-4 | 1000 | 5.0 | 29.32 | 19.25 | 0.56 | 0.50 | 132 |
| OLED4 | 1-5 | 1000 | 4.8 | 30.21 | 20.36 | 0.50, | 0.48 | 111 |
| OLED5 | 2-1 | 1000 | 4.9 | 31.15 | 22.89 | 0.51, | 0.49 | 110 |
| OLED6 | 2-2 | 1000 | 4.5 | 38.56 | 24.25 | 0.49, | 0.45 | 75 |
| OLED7 | 2-3 | 1000 | 5.0 | 28.78 | 20.45 | 0.55, | 0.50 | 121 |
| OLED8 | 2-4 | 1000 | 5.5 | 6.00 | 5.21 | 0.20, | 0.35 | 59 |
| OLED9 | 2-5 | 1000 | 4.8 | 18.26 | 15.23 | 0.22 | 0.40 | 78 |
| OLED10 | 2-6 | 1000 | 5.5 | 8.75 | 17.41 | 0.20 | 0.41 | 62 |
| OLED11 | 2-7 | 1000 | 5.4 | 16.62 | 16.66 | 0.16 | 0.21 | 41 |
| OLED12 | 2-8 | 1000 | 5.3 | 17.12 | 15.91 | 0.17 | 0.21 | 50 |
| OLED13 | 2-9 | 1000 | 5.2 | 18.22 | 15.02 | 0.17, | 0.22 | 52 |

From the above table, it can be seen that the lifetime of the thermally activated delayed fluorescence material containing the heavy atoms of bromine or iodine, as well as the lifetime of the device protected by the invention are both increased, the reason is that reverse intersystem crossing and intersystem crossing of the TADF material are increased through the heavy atom effect, so that the lifetime of triplet excitons is reduced, and ultimately the lifetime of the device is increased.

Embodiments 7-9

The difference between the OLED structure in the embodiments and Embodiment 1 lies in that the host material in the luminescent layer is compound 2-2, and the luminescent dye is Ir(ppy)₃. The doping concentration (weight percentage in the luminescent layer) of Ir(ppy)₃ is 1-10 wt %. ITO/NPB (40 nm)/TCTA (10 nm)/compound 2-2: 1-10 wt % Ir(ppy)₃ (30 nm)/Bphen (40 nm)/LiF (5 nm)/Al Comparative Example 3

The difference between the structure of this Comparative Example and Embodiments 7-9 is only that the host material used for the luminescent layer is CBP:
ITO/NPB (40 nm)/TCTA (10 nm)/CBP: 5 wt % Ir(ppy)₃ (30 nm)/Bphen (40 nm)/LiF (5 nm)/A1

Comparative Example 4

The difference between the structure of this Comparative Example and Embodiments 7-9 is only that the host material used for the luminescent layer is CC2TA:

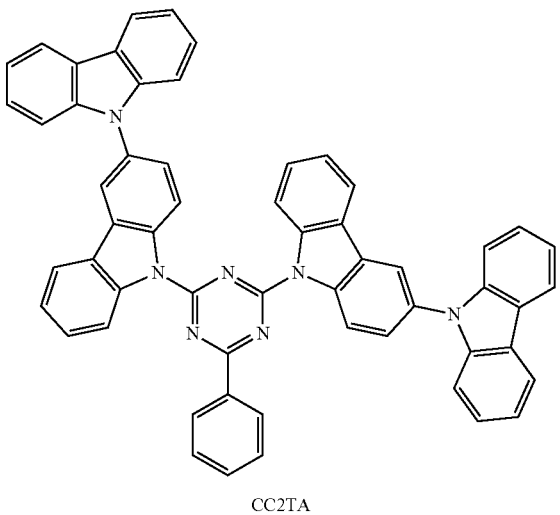

CC2TA

-continued 2-2

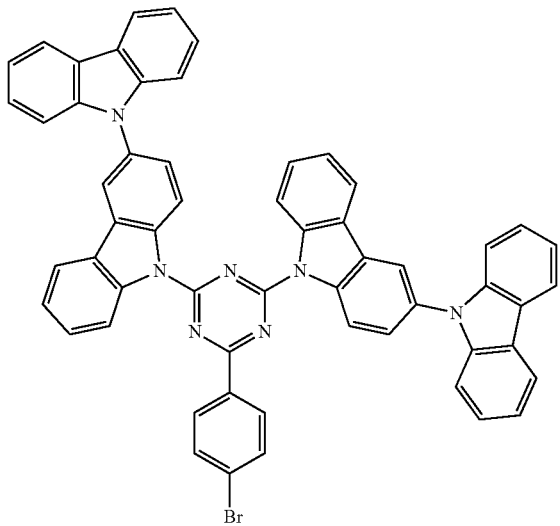

| Serial number | Doping concentration of dye wt % | Luminance cd/m² | Voltage V | Current efficiency cd/A | Lumen efficiency lm/W | x (V) | y (V) | T95 h (at 10000 cd/m²) |
|---|---|---|---|---|---|---|---|---|
| Embodiments 7 | 5 wt % | 1000 | 3.4 | 67 | 91 | 0.27 | 0.63 | 274 |
| Embodiments 8 | 1 wt % | 1000 | 3.0 | 60 | 86 | 0.26 | 0.63 | 260 |
| Embodiments 9 | 10 wt % | 1000 | 4.2 | 59 | 82 | 0.27 | 0.64 | 280 |
| Comparative Example 3 | 5 wt % | 1000 | 5.4 | 45 | 62 | 0.26 | 0.63 | 242 |
| Comparative Example 4 | 5 wt % | 1000 | 3.9 | 62 | 90 | 0.26 | 0.62 | 266 |

From the above table, it can be seen by comparing Embodiment 7, Embodiment 8 and Embodiment 9 with different doping concentrations that the electrical property of the device increases first and then decreases with an increase in the doping concentration of the luminescent dye, and is optimize at the doping concentration of 5 wt %, but the lifetime of the device increases as the doping concentration of the dye increases. In addition, the lifetime of the device protected by the present invention with the thermally activated delayed fluorescence material containing the heavy bromine atoms serving as the host is longer than that of a conventional device with CBP as a host (Comparative Example 3), and comparing with a device with a thermally activated sensitized fluorescent material of the same structure but without heavy atoms serving as a host (Comparative Example 4), the electrical property does not change much, but the lifetime of the device of Example 7 is longer than that of the device of Comparative Example 4, because the reverse intersystem crossing coefficient of the TADF material is increased through the heavy atom effect, so that the lifetime of triplet excitons is reduced, and ultimately the lifetime of the device is increased.

The above-described embodiments are merely preferred embodiments for fully explaining the present invention, and the scope of protection of the present invention is not limited thereto. The equivalent substitutions or alternations that are made by a person skilled in the art on the basis of the present invention all fall within the protection scope of the present invention. The protection scope of the present invention is limited by the claims.

The invention claimed is:

1. A thermally activated delayed fluorescence material, wherein the thermally activated delayed fluorescence material is a compound having a structure shown in formulas 1-2 to 1-5:

1-2

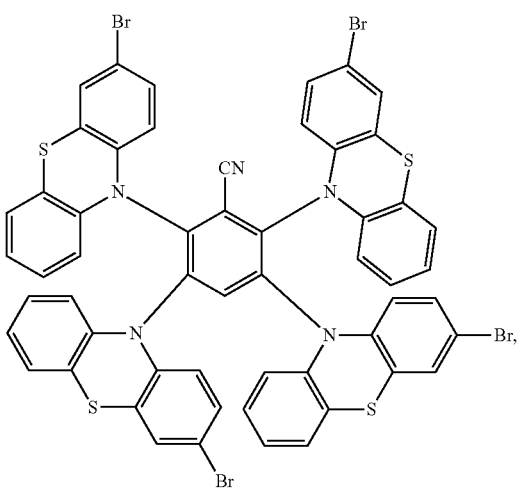

-continued 1-3
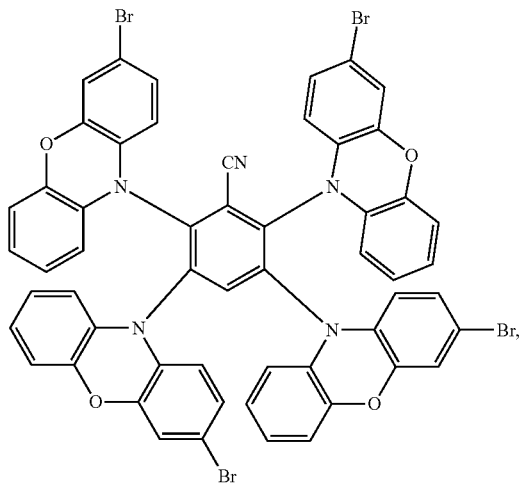

1-4
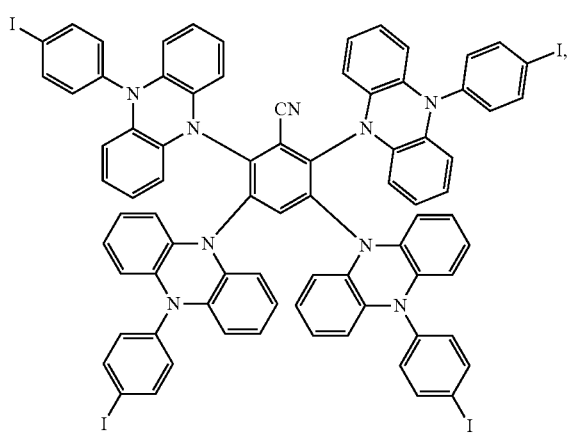

1-5
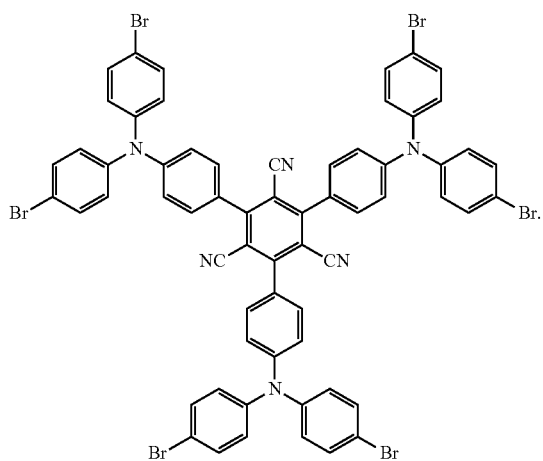

2. An organic electroluminescence device, comprising a luminescent layer, wherein the luminescent layer comprises a host material and a luminescent dye doped in the host material, and one of the host material and the luminescent dye is the thermally activated delayed fluorescence material according to claim 1.

3. The organic electroluminescence device according to claim 2, wherein the luminescent dye is the thermally activated delayed fluorescence material, the luminescent dye accounts for 0.5 wt %-10 wt % of the luminescent layer.

4. The organic electroluminescence device according to claim 2, wherein the luminescent dye is the thermally activated delayed fluorescence material, the luminescent dye accounts for 5 wt % of the luminescent layer.

5. The organic electroluminescence device according to claim 2, wherein the luminescent dye is the thermally activated delayed fluorescence material, the organic electroluminescence device comprises an anode, a hole transport layer, a luminescent layer, an electron transport layer, and a cathode, which are successively deposited on a substrate and are laminated.

6. The organic electroluminescence device according to claim 5, wherein the anode and the hole transport layer has a hole injection layer disposed therebetween.

7. The organic electroluminescence device according to claim 2, wherein the host material is the thermally activated delayed fluorescence material, the luminescent dye accounts for 1 wt %-10 wt % of the luminescent layer.

8. The organic electroluminescence device according to claim 2, wherein the luminescent dye is the thermally activated delayed fluorescence material according to claim 1.

9. An application of the thermally activated delayed fluorescence material according to claim 1, wherein the thermally activated delayed fluorescence material is used as a host material or a luminescent dye of a luminescent layer of an organic electroluminescence device.

\* \* \* \* \*